United States Patent [19]
Lamberts et al.

[11] Patent Number: 4,931,482
[45] Date of Patent: Jun. 5, 1990

[54] USE OF 1,1,1,4,4,4-HEXAEFLUOROBUTANE AS A BLOWING AND INSULATING GAS FOR THE PRODUCTION OF FOAM PLASTICS

[75] Inventors: Wilhelm Lamberts, Cologne; Klaus-Dieter Sommerfeld, Overath; Dietmar Bielefeldt, Ratingen; Albrecht Marhold, Leverkusen; Michael Negele, Cologne, all of Fed. Rep. of Germany

[73] Assignee: Bayer Aktiengesellschaft, Leverkusen, Fed. Rep. of Germany

[21] Appl. No.: 355,530

[22] Filed: May 22, 1989

[30] Foreign Application Priority Data

Jun. 1, 1988 [DE] Fed. Rep. of Germany ....... 3818692

[51] Int. Cl.$^5$ .............................................. C08J 9/14
[52] U.S. Cl. .................................... 521/131; 521/98; 521/908
[58] Field of Search ................................. 521/131, 98

[56] References Cited

U.S. PATENT DOCUMENTS 3,567,788  3/1971  Carr et al. ........................... 260/648

OTHER PUBLICATIONS

Preparation, Properties, and Technology of Fluorine and Organic Fluoro Compounds, C. Slesser and S. R. Schram, (New York, Toronto London: McGraw-Hill Book Company, Inc., 1951), p. 817.

*Primary Examiner*—Morton Foelak
*Attorney, Agent, or Firm*—Joseph C. Gil; Richard E. L. Henderson

[57] ABSTRACT

This invention relates to an improved method of preparing closed cell foams using 1,1,1,4,4,4-hexafluorobutane as a blowing agent and insulating gas in the production of such foams, including isocyanate-based foams such as polyurethane foams and polyisocyanurate foams.

8 Claims, No Drawings

USE OF 1,1,1,4,4,4-HEXAEFLUOROBUTANE AS A BLOWING AND INSULATING GAS FOR THE PRODUCTION OF FOAM PLASTICS

BACKGROUND OF THE INVENTION

This invention relates to the use of 1,1,1,4,4,4-hexafluorobutane (R 356) as an insulating gas and blowing agent for the production of foam plastics, especially isocyanate-based foams and preferably polyurethane foams.

It is known that foams are produced using blowing agents. In closed-cell foams, the blowing agents also act as a o heat-insulating cell gas. The fluorocarbons trichlorofluoromethane (R 11), dichlorodifluoromethane (R 12), trichlorofluoroethane (R 113), and the like, are among the most widely used insulating and blowing gases for foams of polyurethane, polystyrene, polyvinylchloride, phenol-formaldehyde, and others. However, a disadvantage of these halogenated products is their ability, due in part to their high stability, to enter the stratosphere where they are said, because of their chlorine content, to contribute to the degradation of ozone in the stratosphere. For this reason, the world production of chlorofluorocarbons is now limited.

The object of the present invention is to provide insulating gases and blowing agents for the production of foam plastics which cannot damage the ozone layer. This object is achieved by using as the insulating and blowing gas according to the invention, 1,1,1,4,4,4-hexafluorobutane.

SUMMARY OF THE INVENTION

The present invention relates to an improved method of preparing closed cell foams in which a blowing agent is used. The improvement comprises using 1,1,1,4,4,4-hexafluorobutane as o the blowing agent. In such closed cell foams, the blowing agent also serves as an insulating gas. A preferred use of the compound of this invention is in the preparation of isocyanate-based foams, especially polyurethane foams and/or polyisocyanurate foams.

DETAILED DESCRIPTION OF THE INVENTION

In one preferred embodiment of the invention, 1,1,1,4,4,4-hexafluorobutane is used in a quantity of about 2 to about 30% by weight (preferably in a quantity of 2 to 15% by weight and more preferably in a quantity of 2 to 8% by weight) based on the foam plastic.

The production of foam plastics using blowing gases is generally known. The production of isocyanate-based foams is also known and is described, for example, in German Offenlegungsschriften Nos. 1,694,142, 1,694,215 and 1,720,768 and in Kunststoff-Handbuch, Vol VII, "Polyurethane," published by Vieweg and Höchtlen, Carl-Hanser-Verlag, Munich, 1966, and in the new edition of this book edited by G. Oertel, Carl-Hanser-Verlag, Munich/Vienna, 1983.

The foams most commonly used according to this invention are isocyanate-based foams containing urethane, isocyanurate, allophanate, uretdione, urea, or carbodiimide groups, or combinations thereof. The invention is intended primarily for the production of polyurethane and polyisocyanurate foams.

Polyurethane foams according to the invention can be prepared by reacting a polyisocyanate with compounds containing at least two isocyanate-reactive hydrogen atoms in the presence of 1,1,1,4,4,4-hexafluorobutane as blowing agent and insulating gas, optionally in the presence of other components and auxiliaries known in the art.

Suitable materials for the production of the isocyanate-based foams include the following:

1. Isocyanate starting components include aliphatic, cycloaliphatic, araliphatic, aromatic, and heterocyclic polyisocyanates of the type described, for example, by W. Siefken in *Justus Liebigs Annalen der Chemie*, 562, pages 75 to 136. Examples of suitable isocyanates include those corresponding to the formula $$Q(NCO)_n$$

wherein
Q is an aliphatic hydrocarbon group containing about 2 to about 18 (preferably 6 to 10) carbon atoms, a cycloaliphatic hydrocarbon group containing about 4 to about 15 (preferably 5 to 10) carbon atoms, an aromatic hydrocarbon group containing 6 to about 15 (preferably 6 to 13) carbon atoms, or an araliphatic hydrocarbon group containing about 8 to about 15 (preferably 8 to 13) carbon atoms; and
n is a number from about 2 to about 4 (preferably 2-3).

Suitable such isocyanates include polyisocyanates described, for example, in German Offenlegungsschrift No. 2,832,253 at pages 10 and 11. In general, it is particularly preferred to use the commercially readily obtainable polyisocyanates, such as, for example, 2,4- and 2,6-tolylene diisocyanate, and mixtures of these isomers ("TDI"); polyphenyl polymethylene polyisocyanates of the type obtained by phosgenation of aniline-formaldehyde condensates ("crude MDI"); and polyisocyanates containing carbodiimide groups, urethane groups, allophanate groups, isocyanurate groups, urea groups, or biuret groups ("modified polyisocyanates"), particularly modified polyisocyanates which are derived from 2,4- and/or 2,6-tolylene diisocyanate and from 4,4'- and/or 2,4'-diphenylmethane diisocyanate.

2. Other suitable starting components include compounds containing at least two isocyanate-reactive hydrogen atoms and having a molecular weight generally ranging from about 400 to about 10,000. Such compounds may, for example, contain amino groups, thiol groups, carboxyl groups, and, preferably, hydroxyl groups. Preferred compounds of this type contain 2 to 8 hydroxyl groups and have a molecular weight in the range from 1000 to 6000 (preferably in the range from 2000 to 6000). Examples of preferred compounds of this type include polyethers and polyesters containing at least 2 and generally 2 to 8 (but preferably 2 to 6) hydroxyl groups, as well as polycarbonates and polyester amides of the type known for the production of homogeneous and cellular polyurethanes and described, for example, in German Offenlegungsschrift No. 2,832,253, pages 11 to 18.

3. Other optional starting components include compounds containing at least two isocyanate-reactive hydrogen atoms and having a molecular weight in the range from 32 to 399. Compounds of this type may, for example, contain hydroxyl groups, amino groups, thiol groups, or carboxyl groups. Preferred such compounds contain hydroxyl groups and/or amino groups and serve as chain-extending agents or crosslinking agents. These compounds generally contain 2 to 8 (preferably 2 to 4) isocyanate-reactive hydrogen atoms. Examples of such compounds can be found in German Offenlegungsschrift No. 2,832,253, pages 19 to 20.

4. 1,1,1,4,4,4-Hexafluorobutane is used as a blowing and insulating gas.

5. Auxiliaries and additives are optionally used, including
  (a) water and/or other readily volatile organic substances as blowing agents,
  (b) additional known catalysts in quantities of up to about 10% by weight, based on the quantity of the above-described compounds containing at least two isocyanate-reactive hydrogen atoms and having a molecular weight generally ranging from about 400 to about 10,000,
  (c) surface-active additives, such as emulsifiers and foam stabilizers,
  (d) reaction retarders, for example, substances exhibiting an acidic character, such as hydrochloric acid or organic acid halides; known cell regulators, such as paraffins or fatty alcohols or dimethyl polysiloxanes; pigments or dyes; known flameproofing agents, such as tricresyl phosphate; stabilizers against the effects of ageing and weather; plasticizers; fungistatic and bacteriostatic agents; and fillers, such as barium sulfate, kieselguhr, carbon black, or whiting.

These optional auxiliaries and additives are described, for example, in German Offenlegungsschrift No. 2,732,292, pages 21 to 24. Further examples of surface-active additives and foam stabilizers, cell regulators, reaction retarders, stabilizers, flameproofing agents, plasticizers, dyes, fillers, and fungistatic and bacteriostatic agents which may optionally be used in accordance with the invention and information on the use and mode of action of these additives can be found in Kunststoff-Handbuch, Vol VII, published by Vieweg and Höchtlen, Carl-Hanser-Verlag, Munich 1966, for example, on pages 103 to 113.

The isocyanate-based foams are produced by methods known in the art. For example, preparation of polyurethane foams according to the process of this invention may be carried out by the reaction of the various components using the known one-shot process, prepolymer process, or semiprepolymer process. Machines, for example, such as described in U.S. Pat. No. 2,764,565, can often be used to prepare foams according to such processes. Information on processing machines which may be used in accordance with the invention can also be found in Kunststoff-Handbuch, Vol VII, edited by Vieweg and Höchtlen, Carl-Hanser-Verlag, Munich 1966, for example, on pages 121 to 205.

Cold-hardening foams may also be produced in accordance with the invention. See British Pat. No. 1,162,517 and German Offenlegungsschrift No. 2,153,086.

Foams may also be produced by slabstock foaming or by the laminator process.

The products obtainable in accordance with the invention are used, for example, as insulating sheets for roof insulation.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

DESCRIPTION OF THE PREFERRED EMBODIMENTS

I. Preparation of 1,1,1,4,4,4-hexafluorobutane

EXAMPLE A 1,1,1,4,4,4-Hexafluoro-2-chloro-2-butene (40 g) (prepared according to the method described by J. H. Babcock et al in *Preparation, Properties, and Technology of Fluorine and Organic Flyoro Compounds*, eds. C. Slesser and S. R. Schram (New York, Toronto, London: McGraw-Hill Book Company, Inc., 1951) at p. 817) in 300 ml ethanol was hydrogenated in a stainless steel autoclave with hydrogen for 3 hours at 20° C. and for 1 hour at 100° C. in the presence of potassium hydroxide (12 g) and Raney nickel (25 g). The pressure was in the range from 30 to 40 bar. The solid constituents were separated from the reaction mixture by filtration and the filtrate was distilled to give 16 g of 1,1,1,4,4,4-hexafluorobutane, boiling point 25°–30° C. at 1013 mbar. The mass spectrum showed an m+/e of 166.

EXAMPLE B 1,1,1,4,4,4-Hexafluoro-2-chloro-2-butene (199 g, 1 mole) in 800 ml diglyme was hydrogenated in the presence of sodium hydroxide (45 g) and Raney nickel (30 g) at a temperature of 20° to 40° C. and under a pressure of 20 to 40 bar. The solid constituents were filtered off and the filtrate was extracted with water. The organic phase was separated and purified by fractional distillation, giving 125 g (75% of theory) of 1,1,1,4,4,4-hexafluorobutane, boiling point 24°–27° C. at 1013 mbar. The $^{19}$F-nmr spectrum showed a resonance at −10.7 ppm (standard: $CF_3CO_2H$).

EXAMPLE C 1,1,1,4,4,4-Hexafluoro-2-bromo-3-chloro-2-butene (10 g, 36 mmole) in 50 ml tetrahydrofuran was hydrogenated in the presence of sodium hydroxide (3.0 g) and Raney nickel (5 g) at a temperature of 20° to 40° C. and under a hydrogen pressure of 20 to 40 bar. The reaction mixture was worked up as in Example B, producing 3.5 g (59% of theory) of 1,1,1,4,4,4-hexafluorobutane.

EXAMPLE D 1,1,1,4,4,4-Hexafluoro-2-chloro-2-butene in 300 ml ethanol was hydrogenated in the presence of potassium hydroxide (12 g) and Raney nickel (25 g) at a temperature of 20° to 100° C. and under a pressure of 20 to 40 bar. The solid constituents were filtered off and the filtrate was extracted with water. The organic phase was separated and purified by distillation, giving 15.5 g (47% of theory) of 1,1,1,4,4,4-hexafluorobutane, boiling point 24°–27° C. at 1013 bar.

EXAMPLE E

To 1,1,1,4,4,4-hexafluoro-2,3-dichloro-2-butene (23.5 g, 0.1 mole) in 50 ml tetrahydrofuran were added sodium hydroxide (8.5 g) and as catalyst 5% by weight palladium on carbon (3 g). This mixture was hydrogenated with hydrogen at temperatures of 20 to 40° C. under pressures of 20 to 40 bar. The reaction mixture was worked up as in Example B, producing 8.0 g (75% of theory) of 1,1,1,4,4,4-hexafluorobutane.

II Production of polyurethane foams

EXAMPLE 1

100 g of a polyether, hydroxyl value 380, obtained by addition of propylene oxide to a solution of sucrose, propylene glycol, and water,
2 g of a siloxane-polyether copolymer as foam stabilizer,
3.8. g of water, and
3 g of dimethylcyclohexylamine as catalyst
were mixed.
100 g of this mixture were intensively mixed (laboratory stirrer) with
15 g of 1,1,1,4,4,4-hexafluorobutane as blowing agent.
This mixture was foamed with crude 4,4'-diisocyanatodiphenylmethane (152 g) to form a rigid polyurethane foam.

| Foaming and physical data: | |
|---|---|
| Cream time (s) | 10 |
| Gel time (s) | 44 |
| Free gross density (kg/m$^3$) | 25 |
| Cell pattern | fine |

EXAMPLE 2

60 g of a polyether, hydroxyl value 950, obtained by addition of propylene oxide to trimethylolpropane,
40 g of a polyether, hydroxyl value 56, obtained by addition of propylene oxide to trimethylolpropane,
0.5 g of water, and
2 g of a siloxane-polyether copolymer as foam stabilizer
were mixed.
100 g of this mixture were intensively mixed (laboratory stirrer) with
10 g of 1,1,1,4,4,4-hexafluorobutane as blowing agent.
This mixture was foamed with crude 4,4'-diisocyanatodiphenylmethane (164 g) to form a hard polyurethane foam of high gross density.

| Foaming and physical data: | |
|---|---|
| Cream time (s) | 80 |
| Gel time (s) | 130 |
| Free gross density (kg/m$^3$) | 73 |
| Total gross density, compacted (kg/m$^3$) | 350 |
| Cell pattern | fine |

EXAMPLE 3

91 g of a polyether, hydroxyl value 56, obtained by addition of propylene oxide to trimethylolpropane,
9 g of monoethylene glycol, and
0.1 g of water
were mixed.
100 g of this mixture were intensively mixed (laboratory stirrer) with
15 - g of 1,1,1,4,4,4-hexafluorobutane as blowing agent.
This mixture was foamed with crude 4,4'-diisocyanatodiphenylmethane (56 g) to form a tough and resilient polyurethane foam.

| Foaming and physical data: | |
|---|---|
| Cream time (s) | 35 |
| Gel time (s) | 105 |
| Free gross density (kg/m$^3$) | 127 |
| Cell pattern | fine |

EXAMPLE 4

100 g of a polyether, hydroxyl value 56, obtained by addition of propylene oxide to trimethylolpropane,
3 g of water,
1 g of a siloxane-polyether copolymer as foam stabilizer, and
0.05 g of dibutyl tin dilaurate
were mixed.
100 g of this mixture were intensively mixed (laboratory stirrer) with
10 g of 1,1,1,4,4,4-hexafluorobutane as blowing agent.
This mixture was foamed with tolylene diisocyanate (41 g) to form a flexible polyurethane foam.

| Foaming and physical data: | |
|---|---|
| Cream time (s) | 7 |
| Gel time (s) | 100 |
| Free gross density (kg/m$^3$) | 27 |
| Cell pattern | fine |

What is claimed is:

1. In a method of producing an isocyanate-based polymer closed cell foam wherein a blowing agent is used, the improvement comprising using 1,1,1,4,4,4-hexafluorobutane as the blowing agent.

2. A method according to claim 1 wherein 1,1,1,4,4,4-hexafluorobutane is used in a quantity of 2 to 30% by weight, based on the foam.

3. A method according to claim 1 wherein 1,1,1,4,4,4-hexafluorobutane is used in a quantity of 2 to 15% by weight, based on the foam.

4. A method according to claim 1 wherein 1,1,1,4,4,4-hexafluorobutane is used in a quantity of 2 to 8% by weight, based on the foam.

5. A method according to claim 1 wherein the foam is a polyurethane foam.

6. A method according to claim 1 wherein the foam is a polyisocyanurate foam.

7. A method of preparing a polyurethane foam comprising reacting a polyisocyanate with a compound containing at least two isocyanate-reactive hydrogen atoms in the presence of 1,1,1,4,4,4-hexafluorobutane as a blowing agent and insulating gas.

8. A method according to claim 7 wherein the 1,1,1,4,4,4-hexafluorobutane is used in a quantity of 2 to 8% by weight, based on the polyurethane foam.

* * * * *